US012661512B2

(12) United States Patent
Agnesi et al.

(10) Patent No.: US 12,661,512 B2
(45) Date of Patent: *Jun. 23, 2026

(54) NEUROSTIMULATION USING ONE OR MORE CYCLING PARAMETERS FOR A NON-PARESTHESIA STIMULATION PATTERN

(71) Applicant: Advanced Neuromodulation Systems, Inc., Plano, TX (US)

(72) Inventors: Filippo Agnesi, Plano, TX (US); Lalit Venkatesan, Propser, TX (US); Christopher S. L. Crawford, Sunnyvale, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,067

(22) Filed: Apr. 23, 2024

(65) Prior Publication Data

US 2025/0099765 A1 Mar. 27, 2025

Related U.S. Application Data

(63) Continuation of application No. 16/404,517, filed on May 6, 2019, now Pat. No. 11,964,152.

(51) Int. Cl.
*A61N 1/36* (2006.01)
*A61N 1/06* (2006.01)
*A61N 1/372* (2006.01)

(52) U.S. Cl.
CPC ........... *A61N 1/36071* (2013.01); *A61N 1/06* (2013.01); *A61N 1/36062* (2017.08); *A61N 1/36167* (2013.01); *A61N 1/37247* (2013.01)

(58) Field of Classification Search
CPC ............ A61N 1/36071; A61N 1/36062; A61N 1/36167; A61N 1/36128; A61N 1/36178
See application file for complete search history.

(56) References Cited

U.S. PATENT DOCUMENTS 6,516,227 B1 2/2003 Meadows et al.
8,606,362 B2 12/2013 He et al.
(Continued)

FOREIGN PATENT DOCUMENTS

WO WO-2020162990 A2 8/2020
WO WO-2020251899 A1 12/2020
WO WO-2021003290 A1 1/2021

OTHER PUBLICATIONS

Moorman BA. Service models for remote healthcare monitoring systems. Biomed Instrum Technol. 2010; Suppl Home Healthcare: 64-8. PMID: 22049611. (Year: 2010).*
(Continued)

*Primary Examiner* — Niketa Patel
*Assistant Examiner* — Skylar Lindsey Christianson
(74) *Attorney, Agent, or Firm* — Norton Rose Fulbright US LLP

(57) ABSTRACT

This application is generally related to identifying or otherwise programming one or more cycling parameters for operation of an implantable pulse generator to provide a neurostimulation therapy to a patient using a non-paresthesia stimulation pattern. In some embodiments, the cycling parameter is selected by measuring physiological signals during trial stimulation. In other embodiments, multiple cycling parameters are identified for use by the patient using a patient controller device.

20 Claims, 14 Drawing Sheets

(56) References Cited

U.S. PATENT DOCUMENTS

| | | | |
|---|---|---|---|
| 8,620,436 | B2 | 12/2013 | Parramon et al. |
| 9,492,667 | B1 | 11/2016 | Kent et al. |
| 10,576,282 | B2 | 3/2020 | Doan et al. |
| 2005/0065575 | A1 | 3/2005 | Dobak |
| 2009/0082640 | A1 | 3/2009 | Kovach et al. |
| 2009/0083070 | A1 | 3/2009 | Giftakis et al. |
| 2013/0066411 | A1 | 3/2013 | Thacker et al. |
| 2013/0282078 | A1 | 10/2013 | Wacnik |
| 2014/0222106 | A1 | 8/2014 | Sharma et al. |
| 2014/0277259 | A1 | 9/2014 | Rosenberg et al. |
| 2014/0364919 | A1 | 12/2014 | Doan |
| 2015/0190634 | A1 | 7/2015 | Rezai et al. |
| 2015/0217117 | A1 | 8/2015 | Hershey |
| 2015/0231402 | A1 | 8/2015 | Aghassian |
| 2015/0360038 | A1 | 12/2015 | Zottola et al. |
| 2016/0022988 | A1 | 1/2016 | Thieme et al. |
| 2016/0022997 | A1 | 1/2016 | Bonnet et al. |
| 2016/0129272 | A1 | 5/2016 | Hou et al. |
| 2016/0144183 | A1 | 5/2016 | Marnfeldt |
| 2016/0206883 | A1* | 7/2016 | Bornzin ............. A61N 1/36182 |
| 2016/0250472 | A1 | 9/2016 | Carbunaru |
| 2017/0165491 | A9 | 6/2017 | De Ridder |
| 2017/0266455 | A1 | 9/2017 | Steinke |
| 2017/0348530 | A1 | 12/2017 | Doan et al. |
| 2018/0071513 | A1 | 3/2018 | Weiss et al. |
| 2018/0167482 | A1 | 6/2018 | Gliner et al. |
| 2018/0169373 | A1 | 6/2018 | Tass et al. |
| 2018/0229041 | A1 | 8/2018 | Pepin et al. |
| 2018/0369592 | A1 | 12/2018 | Johanek |
| 2019/0046800 | A1 | 2/2019 | Doan et al. |
| 2020/0046987 | A1* | 2/2020 | Cantua ............... A61N 1/36171 |
| 2020/0147400 | A1 | 5/2020 | Moffitt et al. |
| 2020/0384270 | A1 | 12/2020 | Doan et al. |

OTHER PUBLICATIONS

USPTO, Office Action, U.S. Appl. No. 16/404,477, Dec. 22, 2020, 11 pgs.

Barts & The London NHS Trust, "A High Frequency Spinal Cord Stimulation PET-CT Scan Study," 7 pgs., uploaded Oct. 23, 2018; https://clinicaltrials.gov/ct2/show/NCT03716557.

Moorman, B. A. Service models for remote healthcare monitoring systems. Biomed Instrum Technol. 2010; Suppl Home Healthcare: 64-8. PMID: 22049611.

Patent Cooperation Treaty, International Search Report and Written Opinion issued for PCT Application No. PCT/US2020/029009, dated Jul. 20, 2020, 7 pages.

Patent Cooperation Treaty, International Search Report and Written Opinion issued for PCT Application No. PCT/US2020/029332, dated Jul. 20, 2020, 7 pages.

How long do you use a tens machine for. TENS Pros. (2016). Retrieved Feb. 28, 2023, from https://www.tenspros.com/How-Long-Do-You-Use-a-TENS-Machine-For_b_18.html (Year: 2016).

European Patent Office, Communication, Extended European Search Report issued for European Patent Application No. 20801660.0, dated Dec. 14, 2022, 7 pages.

European Patent Office, Communication, Extended European Search Report issued for European Patent Application No. 24153272.0, dated Feb. 27, 2024, 6 pages.

* cited by examiner

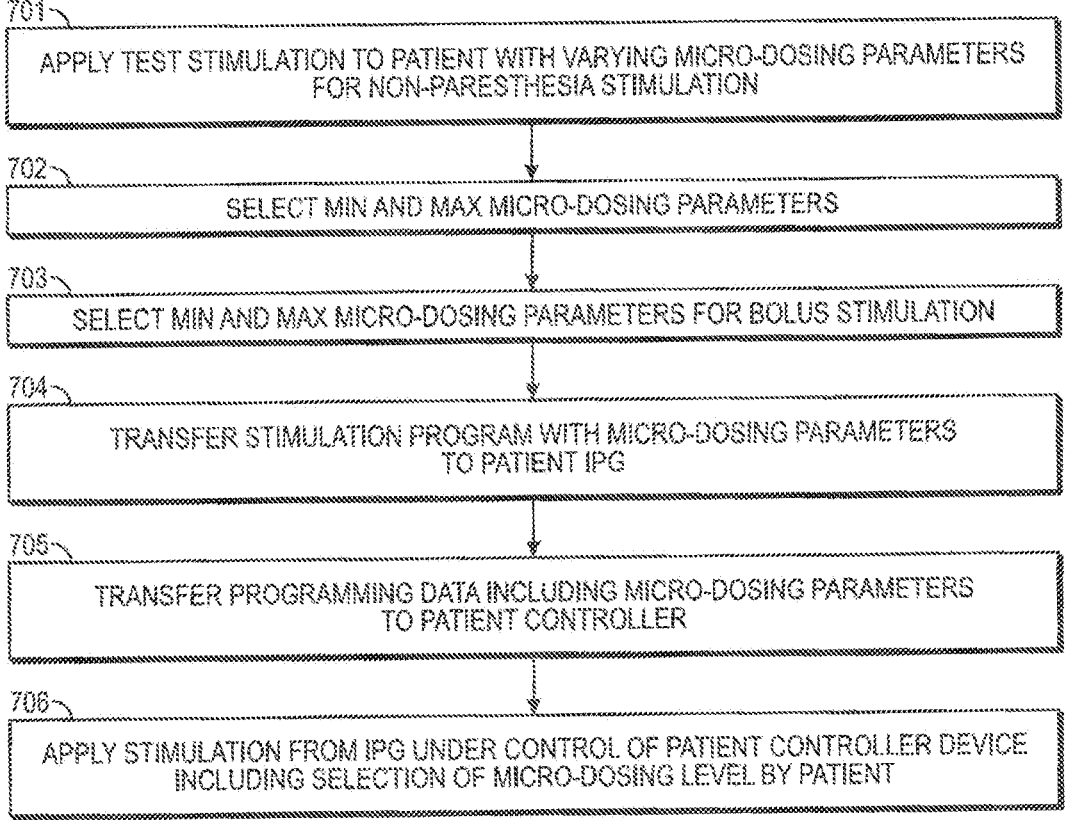

701 — APPLY TEST STIMULATION TO PATIENT WITH VARYING MICRO-DOSING PARAMETERS FOR NON-PARESTHESIA STIMULATION

702 — SELECT MIN AND MAX MICRO-DOSING PARAMETERS

703 — SELECT MIN AND MAX MICRO-DOSING PARAMETERS FOR BOLUS STIMULATION

704 — TRANSFER STIMULATION PROGRAM WITH MICRO-DOSING PARAMETERS TO PATIENT IPG

705 — TRANSFER PROGRAMMING DATA INCLUDING MICRO-DOSING PARAMETERS TO PATIENT CONTROLLER

706 — APPLY STIMULATION FROM IPG UNDER CONTROL OF PATIENT CONTROLLER DEVICE INCLUDING SELECTION OF MICRO-DOSING LEVEL BY PATIENT

FIG. 7

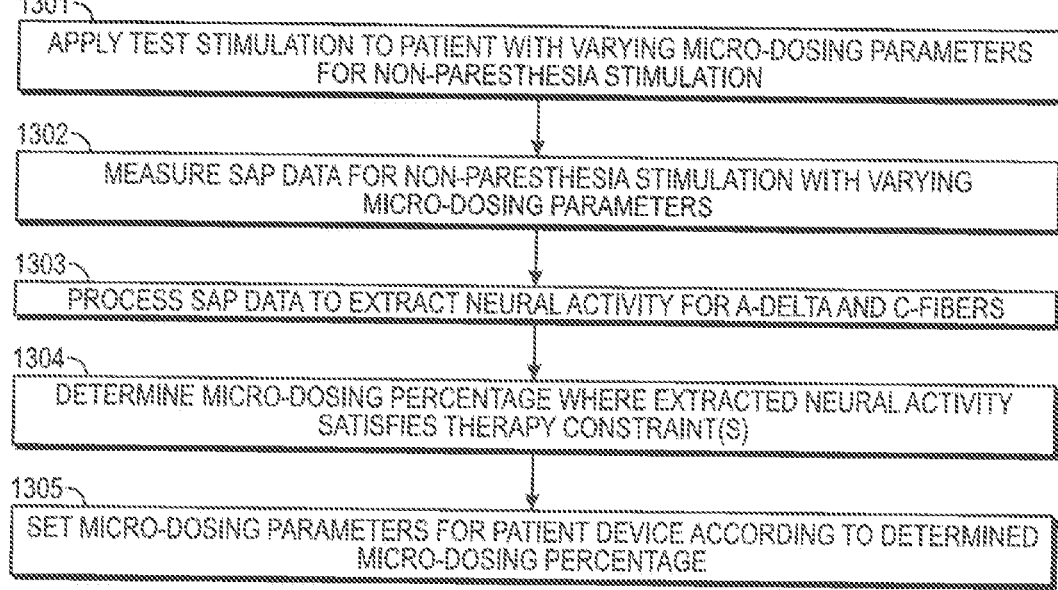

1301 APPLY TEST STIMULATION TO PATIENT WITH VARYING MICRO-DOSING PARAMETERS FOR NON-PARESTHESIA STIMULATION

1302 MEASURE SAP DATA FOR NON-PARESTHESIA STIMULATION WITH VARYING MICRO-DOSING PARAMETERS

1303 PROCESS SAP DATA TO EXTRACT NEURAL ACTIVITY FOR A-DELTA AND C-FIBERS

1304 DETERMINE MICRO-DOSING PERCENTAGE WHERE EXTRACTED NEURAL ACTIVITY SATISFIES THERAPY CONSTRAINT(S)

1305 SET MICRO-DOSING PARAMETERS FOR PATIENT DEVICE ACCORDING TO DETERMINED MICRO-DOSING PERCENTAGE

FIG. 13

NEUROSTIMULATION USING ONE OR MORE CYCLING PARAMETERS FOR A NON-PARESTHESIA STIMULATION PATTERN

CROSS-REFERENCE TO RELATED APPLICATIONS

The present application is a continuation of U.S. patent application Ser. No. 16/404,517 filed May 6, 2019 and entitled "NEUROSTIMULATION USING ONE OR MORE CYCLING PARAMETERS FOR A NON-PARESTHESIA STIMULATION PATTERN," the disclosure of which is incorporated by reference herein in its entirety.

BACKGROUND

In 1959, neurosurgeon Willem Noordenbos reported that a signal carried along large diameter fibers may inhibit the signal carried by the thinner pain fibers. From this, Melzack and Wall proposed the "Gate-control" theory of pain. The Gate-control theory postulates that stimulation of large myelinated fibers suppresses the response of dorsal horn neurons to input from small, unmyelinated peripheral pain fibers. The Gate-control theory provided the theoretical foundation for the use of spinal cord stimulation (SCS) as a clinical treatment for chronic pain. The first experimental clinical use of SCS was shortly followed by clinical trials of SCS in patients suffering from intractable chronic pain in the early seventies.

In conventional SCS, an electrode is positioned over the spinal cord and connected to an internal pulse generator. Conventional pulse generators deliver tonic pulses that can be modified by altering the pulse width, frequency, and amplitude to define the patient therapy. The internal pulse generators can use either constant voltage or constant current to modulate the underlying cells or networks. Electrical stimulation of large afferents of the dorsal column by an electrode placed dorsomedially in the epidural space elicits a tingling sensation (paresthesia) in the corresponding dermatomes. To obtain successful treatment of chronic neuropathic pain by conventional SCS, the stimulation-induced paresthesia must cover the pain area completely.

More recent SCS therapies have been applied to address chronic pain in patients. One example is BurstDR™ stimulation (available in SCS systems of Abbott, Plano TX). This type of SCS has been reported to address chronic pain in patients without necessarily inducing paresthesia in patients. De Ridder D., Vanneste S., Plazier M, van der Loo E, Menovsky T., Burst Spinal Cord Stimulation: Toward Paresthesia-Free Pain Suppression, Neurosurgery 2010; 66:986-90.

Dorsal root ganglion (DRG) stimulation is another neurostimulation method that has been recently developed for use for chronic pain. The DRG is a neural structure located at each segmental level of the spinal column in the lateral epidural space within the spinal foramen. The DRG contains the cell bodies of the primary sensory neurons. The DRG is involved in the transduction of pain to the central nervous system. It has been experimentally shown that electrical stimulation of the DRG reduces the excitability of the DRG neurons. It has been reported that incoming afferent pain signals spread over the different levels of the spinal cord and dorsal root ganglia and as a consequence communication between the segmental levels takes effect. The possible advantages of DRG stimulation include an improved ability to achieve pain relief in locations that are typically challenging to effectively achieve with SCS and enhanced stability of the stimulation regardless of body position.

SUMMARY

Representative embodiments are directed to systems and methods for programming and/or delivering a non-paresthesia neurostimulation therapy to treat chronic pain of a patient using one or more cycling parameters. The one or more cycling parameters may include a stimulation-on interval length of time, a stimulation-off interval length of time, a duty cycle ratio or percentage, and/or the like. The cycling parameters define interleaved stimulation-on intervals and stimulation-off intervals for delivery of a non-paresthesia stimulation pattern. In some embodiments, the non-paresthesia stimulation pattern may be a burst stimulation pattern or a high-frequency stimulation pattern (e.g., a frequency of 1200 Hz, 10,000 Hz, or more). In some embodiments, the stimulation-on intervals and stimulation-off intervals are longer than one second.

In some embodiments, a method of selecting parameters for a non-paresthesia stimulation therapy for a patient comprises: applying electrical stimulation to a peripheral site of the patient; applying electrical spinal cord stimulation to the patient using respective non-paresthesia stimulation patterns with multiple different cycling parameters while the electrical stimulation is applied to the peripheral site of the patient; measuring a respective patient physiological response using electrocorticography (EEG) electrodes for electrical stimulation for each different cycling parameter; identifying at least one cycling parameter based on the measured patient physiological responses; and programming an implantable pulse generator of the patient to provide non-paresthesia stimulation using stimulation-on intervals and stimulation-off intervals that have respective lengths that correspond to the at least one cycling parameter. In some embodiments, the patient physiological response includes somatosensory evoked potentials measured using the EEG electrodes.

In some embodiments, the method further comprises applying electrical stimulation using a reference non-paresthesia stimulation pattern and comparing a physiological response for the reference non-paresthesia stimulation to the physiological responses measured for the different cycling parameters. In some embodiments, the reference non-paresthesia stimulation pattern is a stimulation pattern without interleaved stimulation-on intervals and stimulation-off intervals. In some embodiments, the reference non-paresthesia stimulation pattern is a stimulation pattern previously determined to provide optimal pain relief.

In some embodiments, the identifying at least one cycling parameter based on the measured patient physiological responses comprises: determining a lowest cycling ratio that exhibits a measured physiological response that is statistically equivalent to the measured physiological response for the reference non-paresthesia stimulation pattern. In some embodiments, the electrical stimulation applied to a peripheral site of the patient produces a muscle twitch in the patient. In some embodiments, the electrical stimulation is applied to a peripheral site of the patient that is ipsilateral to a location of chronic pain of the patient. In other embodiments, the electrical stimulation is applied to a peripheral site of the patient that is contralateral to a location of chronic pain of the patient.

In some embodiments, a method of selecting parameters for a non-paresthesia stimulation therapy for a patient, wherein the method is performed by a clinician programmer device comprises: applying electrical spinal cord stimulation to the patient using respective non-paresthesia stimulation patterns with multiple different cycling parameters by communicating stimulation parameters to an implantable pulse generator of the patient; receiving sensing sensory action potential (SAP) data from the implantable pulse generator, wherein the SAP data is obtained from sensory action potentials evoked in response to the applied electrical stimulation using respective non-paresthesia stimulation patterns with multiple different cycling parameters; identifying at least one cycling parameter based on the measured patient physiological responses; and programming an implantable pulse generator of the patient to provide non-paresthesia stimulation using stimulation-on intervals and stimulation-off intervals that correspond to the at least one cycling parameter. In some embodiments, the evoked SAPs are measured using electrodes of a stimulation lead used to apply electrical spinal cord stimulation to the patient.

In some embodiments, the method further comprises: applying electrical stimulation using a reference non-paresthesia stimulation pattern and comparing SAP data for the reference non-paresthesia stimulation to the SAP data measured for the different cycling parameters. In some embodiments, the reference non-paresthesia stimulation pattern is a stimulation pattern without interleaved stimulation-on intervals and stimulation-off intervals. In some embodiments, the reference non-paresthesia stimulation pattern is a stimulation pattern previously determined to provide optimal pain relief.

In some embodiments, the identifying at least one cycling parameter comprises: determining power corresponding to A-delta and C-fibers for SAP data for the reference non-paresthesia stimulation to the SAP data measured for the different cycling parameters; and identifying a lowest one cycling parameter that has power corresponding to A-delta and C-fibers that differs within a predetermined amount from power corresponding to A-delta and C-fibers in SAP data for the reference non-paresthesia stimulation.

In some embodiments, a method of providing a neurostimulation therapy to a patient using a non-paresthesia stimulation pattern comprises: communicating one or more first control signals from a patient controller device to an implantable pulse generator to provide stimulation pulses for a regular mode of stimulation; operating the implantable pulse generator, in response to the one or more first control signals, to apply stimulation pulses to nerve tissue of the patient using the non-paresthesia stimulation pattern with interleaved stimulation-on intervals and stimulation-off intervals that correspond to a first cycling parameter for the regular mode of stimulation; communicating one or more second control signals from the patient controller device to the implantable pulse generator to provide stimulation pulses for a bolus mode of stimulation; and operating the implantable pulse generator, in response to the one or more second control signals, to apply stimulation pulses to nerve tissue of the patient using the non-paresthesia stimulation pattern with interleaved stimulation-on intervals and stimulation-off intervals that correspond to a second cycling parameter for the bolus mode of stimulation, wherein the second cycling parameter provides greater relative provision of pulses of the non-paresthesia stimulation pattern than the first cycling parameter.

In some embodiments, the patient controller device provides one or more user interface controls to allow the patient to select the first cycling parameter from a range of permitted values. In some embodiments, the patient controller device provides one or more user interface controls to allow the patient to select the second cycling parameter from a range of permitted values.

In some embodiments, the bolus mode of operation is limited to a predetermined amount of time. In some embodiments, the implantable pulse generator automatically reverts to the regular mode of operation from the bolus mode of operation at an end of the predetermined amount of time.

In some embodiments, the patient controller device limits a number of episodes of bolus mode of stimulation per day according to a clinician parameter. In some embodiments, the patient controller device communicates a signal to a remote care network or a clinician system that a patient has selected a number of bolus episodes.

In some embodiments, a system for providing a neurostimulation therapy to a patient using a non-paresthesia stimulation pattern comprises: an implantable pulse generator (IPG) for providing stimulation pulses to tissue of the patient using a non-paresthesia stimulation pattern, the IPG comprising: a processor for controlling operations of the IPG, pulse generating circuitry, and wireless communication circuitry; and a patient controller device for communicating with the IPG to control provision of the neurostimulation therapy to the patient, wherein the patient controller device comprises: a processor for controlling the patient controller device, wireless communication circuity for communicating with the IPG, and one or more user interface components for interacting with the patient; wherein the patient controller device is adapted to receive first input from the patient to control the neurostimulation therapy according to a regular mode of operation and, in response to receiving the first input, to communicate one or more first control signals from a patient controller device to the IPG to provide stimulation pulses for the regular mode of stimulation using the non-paresthesia stimulation pattern with interleaved stimulation-on intervals and stimulation-off intervals that correspond to a first cycling parameter; wherein the patient controller device is adapted to receive second input from the patient to control the neurostimulation therapy according to a bolus mode of operation and, in response to receiving the second input, to communicate one or more second control signals from a patient controller device to the IPG to provide stimulation pulses for the bolus mode of stimulation using the non-paresthesia stimulation pattern with interleaved stimulation-on intervals and stimulation-off intervals that correspond to a second cycling parameter; wherein the second cycling parameter provides greater relative provision of pulses of the non-paresthesia stimulation pattern than the first cycling parameter.

In some embodiments, the patient controller device provides one or more user interface controls to allow the patient to select the first cycling parameter from a range of permitted values. In some embodiments, the patient controller device provides one or more user interface controls to allow the patient to select the second cycling parameter from a range of permitted values.

In some embodiments, the bolus mode of operation is limited to a predetermined amount of time. In some embodiments, the IPG automatically reverts to the regular mode of operation from the bolus mode of operation at an end of the predetermined amount of time.

In some embodiments, the patient controller device limits a number of episodes of bolus mode of stimulation per day according to a clinician parameter. In some embodiments, the patient controller device communicates a signal to a remote care network or a clinician system that a patient has selected a number of bolus episodes.

BRIEF DESCRIPTION OF THE DRAWINGS

FIG. 7 depicts a flowchart for providing a neurostimulation therapy using a non-paresthesia stimulation pattern according to some embodiments.

FIG. 13 depicts a flowchart for selecting parameters for a neurostimulation therapy using a non-paresthesia stimulation pattern according to some embodiments.

DETAILED DESCRIPTION

Figure 1:
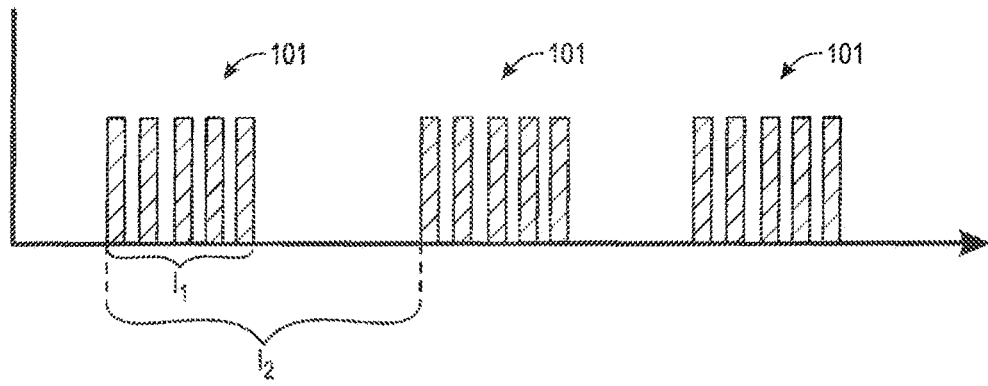
FIG. 1 depicts a non-paresthesia stimulation pattern that may be configured for a patient according to some embodiments.

Traditional spinal cord stimulation and neurostimulation therapies apply electrical stimulation to respective neural targets to induce the patient's perception of paresthesia in regions of the body where the patient perceives chronic pain. Paresthesia is often described as a tingling sensation or prickling sensation, although other sensory experiences may also be present such as buzzing, burning, throbbing, etc. While most patients are tolerant of the sensation, some find the tingling sensation so overwhelming that they turn off their SCS device. This side-effect significantly compromises patient compliance and confidence with traditional SCS treatment.

Advances in the clinical application of spinal cord stimulation and neurostimulation have occurred in recent years including the development of stimulation patterns that do not cause the patient to experience paresthesia. One example of stimulation without paresthesia is the burst stimulation pattern described by Dr. De Ridder in Burst Spinal Cord Stimulation: Toward Paresthesia-Free Pain Suppression: Neurosurgery 66:986-990, 2010. This type of stimulation is available in commercially available neurostimulation products (Prodigy™, and Protege™ IPGs from Abbott, Plano TX). Also, "high frequency" sub-perception stimulation has been applied to patients to treat chronic pain as described by Al-Kaisy A., Van Buyten J. P., Smet I., Palmisani S., Pang D., Smith T., Sustained effectiveness of 10 kHz high-frequency spinal cord stimulation for patients with chronic, low back pain: 24-month results of a prospective multicenter study. Pain Med 2014; 15 347-354. These references are incorporated herein by reference.

The differences in traditional neurostimulation and non-paresthesia neurostimulation cause differences in programming the neurostimulation parameters for patients. In traditional neurostimulation, "perception" and "maximum tolerable" thresholds are determined. The perception threshold is the level (generally largely determined by the pulse amplitude) at which the patient consciously perceives stimulation (e.g., when paresthesia is first noticed). The maximum tolerable threshold is the highest level (typically pulse amplitude) of stimulation at which the patient is able to tolerate the paresthesia. The patient SCS system is programmed to allow stimulation to occur between these levels. The patient may increase or decrease the stimulation level (pulse amplitude) at the patient's discretion. Largely, the patient is instructed to increase the stimulation level to experience greater pain relief from SCS when necessary.

In contrast, the stimulation level for non-paresthesia neurostimulation is selected to remain below the perception threshold. It has also been suggested to use analysis of evoked compound action potentials to select the appropriate amplitude level (see U.S. Patent Application Pub. No. 2017/0259074, entitled "SYSTEM AND METHOD TO CONTROL A NON-PARESTHESIA STIMULATION BASED ON SENSORY ACTION POTENTIALS," which is incorporated herein by reference) for non-paresthesia stimulation where the stimulation level remains below the perception threshold.

Although non-paresthesia neurostimulation has been shown to offer clinical benefits for patients, additional refinement of non-paresthesia neurostimulation may benefit patient outcomes. For example, a given patient's experience of chronic pain at any point in time may depend on a number of dynamically changing internal and external factors. The factors may include diverse physical and psychological influences. In contrast to conventional neurostimulation, simply increasing the stimulation level is not necessarily an effective means for a patient to experience greater pain relief from non-paresthesia stimulation because an increase in amplitude may cause the neurostimulation to exceed the perception threshold and cause the patient to perceive paresthesia.

It has been demonstrated that micro-dosing of burst stimulation can provide clinically equivalent results to standard BurstDR™ stimulation parameters while substantially reducing battery consumption. (Therapeutic Efficacy of BurstDR™ Micro-dosing in Treatment of Chronic Pain, presented at 16th Annual Pain Medicine Meeting, which is incorporated herein by reference). Micro-dosing refers to a method of applying stimulation-on and stimulation-off times to the stimulation pattern. In the applicable study, patients were subjected to continuous burst stimulation (5 pulses per burst, 500 Hz intraburst frequency, 40 Hz interburst frequency, 1000 μs pulse width), burst stimulation (same parameters as continuous stimulation) on for 5 seconds and no stimulation for 5 seconds in repeated cycles, and burst stimulation (same parameters as continuous stimulation) is on for 5 seconds and no stimulation for 10 seconds in repeated cycles. Micro-dosing may be equivalently referred to as cycling and the selected on/off times define the duty cycle of the applied stimulation.

FIG. 1 depicts non-paresthesia stimulation that may be applied to a patient according to one embodiment. The non-paresthesia stimulation includes a plurality of bursts 101 with adjacent bursts 101 separated by a quiescent period therebetween. The pulses of each burst 101 in FIG. 1 are monophasic pulses. Charge balancing occurs during the quiescent period (i.e., charge build up due to capacitance is discharged). Each bursts 101 includes five (5) pulses that occur at a given pulse rate for a burst duration ($I_1$). The burst interval ($I_2$) is defined as the time from the beginning of the first pulse of a given burst 101 to the beginning of the first pulse of the next subsequent burst 101. The burst repetition rate is calculated as the inverse of the burst interval ($1/I_2$). The various parameters may be selected within suitable bounds so that the patient does not experience paresthesia. The parameters may include the following values: 5 pulses per burst, 500 Hz intraburst frequency, 40 Hz interburst frequency, and 1000 µs pulse width with the pulse amplitude selected to maintain the stimulation below a level where paresthesia is experienced. Although these parameters may be selected for one embodiment, other stimulation parameters may be selected as long as the patient does not experience paresthesia.

In other embodiments, the non-paresthesia stimulation may be "high frequency" stimulation or "high density" stimulation. In high frequency stimulation, a substantially continuous train of biphasic, charge balanced pulses are applied at a high frequency (e.g., 1500 Hz to 50,000 Hz). In "high density" stimulation, a similar pattern is applied at somewhat lower frequencies (e.g., about 1200 Hz)—see Paresthesia-Free High-Density Spinal Cord Stimulation for Postlaminectomy Syndrome in a Prescreened Population: A Prospective Case Series, Jennifer Sweet, MD; Anish Badjatiya, BS; Daniel Tan, PhD; Jonathan Miller, MD, Neuromodulation 2016: 19; pp 260-267, which is incorporated herein by reference.

Figure 2:
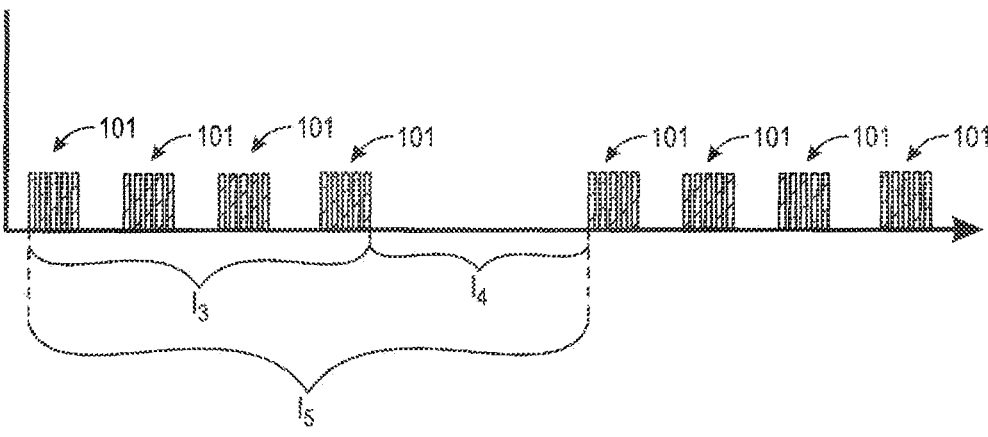
FIG. 2 depicts a non-paresthesia stimulation pattern that may be configured for a patient according to some embodiments.

FIG. 2 depicts micro-dosing or cycling stimulation that may be applied to a patient according to some embodiments. Stimulation is applied in repeated on and off stimulation intervals in a cyclical manner. The on stimulation interval has a duration of $I_3$ and the off stimulation interval has a duration of $I_4$. The duty cycle of the micro-dosing stimulation is $I_3/I_5$ where $I_5 = I_3 + I_4$. Although FIG. 2 depicts cycling of burst stimulation, the cycling may be applied to any non-paresthesia stimulation according to other embodiments including "high frequency" stimulation and "high density" stimulation.

Figures 14, 15:
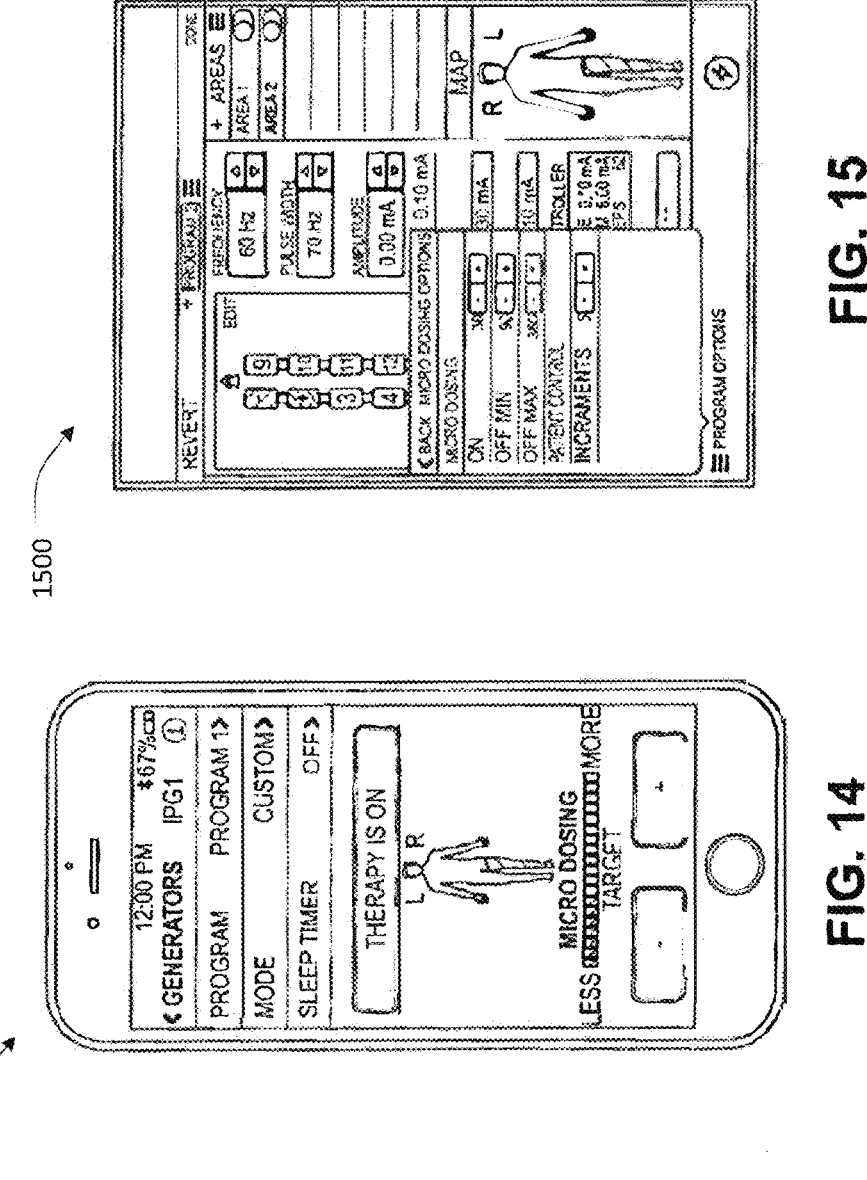
FIGS. 14 and 15 depict respective user interfaces for controlling and programming non-paresthesia stimulation according to some embodiments.

In some embodiments, a neurostimulation system is adapted to vary the cycling of non-paresthesia stimulation according to a patient's perception of pain at a given time. As the patient experiences a greater degree of pain, the patient may increase the duty cycle to obtain greater pain relief while maintaining the stimulation level below the perception threshold. FIGS. 14 and 15 depict respective user interfaces for controlling and programming non-paresthesia stimulation according to some embodiments. FIG. 14 depicts user interface 1400 (which may be provided by a patient controller device) to allow a patient to control non-paresthesia stimulation. User interface 1400 includes graphical user interface controls that permit the user to increase or decrease the duty cycle applied to the provision of the non-paresthesia stimulation by the patient's implantable pulse generator within limits defined by a clinician. FIG. 15 depicts user interface 1500 (which may be provided by a clinician programmer device) to allow a clinician to program a non-paresthesia stimulation program for a patient. User interface 1500 includes graphical user interface controls that permit the clinician to define duty cycle minimum and maximum values to be applied to the micro-dosing control of the duty cycle for the patient's non-paresthesia stimulation. In some embodiments, the clinician defines a length of time for the "on" stimulation period for the cycling. The clinician also defines minimum and maximum lengths of time for the "off" stimulation period. The clinician may define the "increment" value which is the step size applied from the minimum and maximum "off" period limits. The patient may increase and/or decrease (using user interface 1400) the length of the "off" period between the minimum and maximum off limits according to the defined step size.

Figure 3:
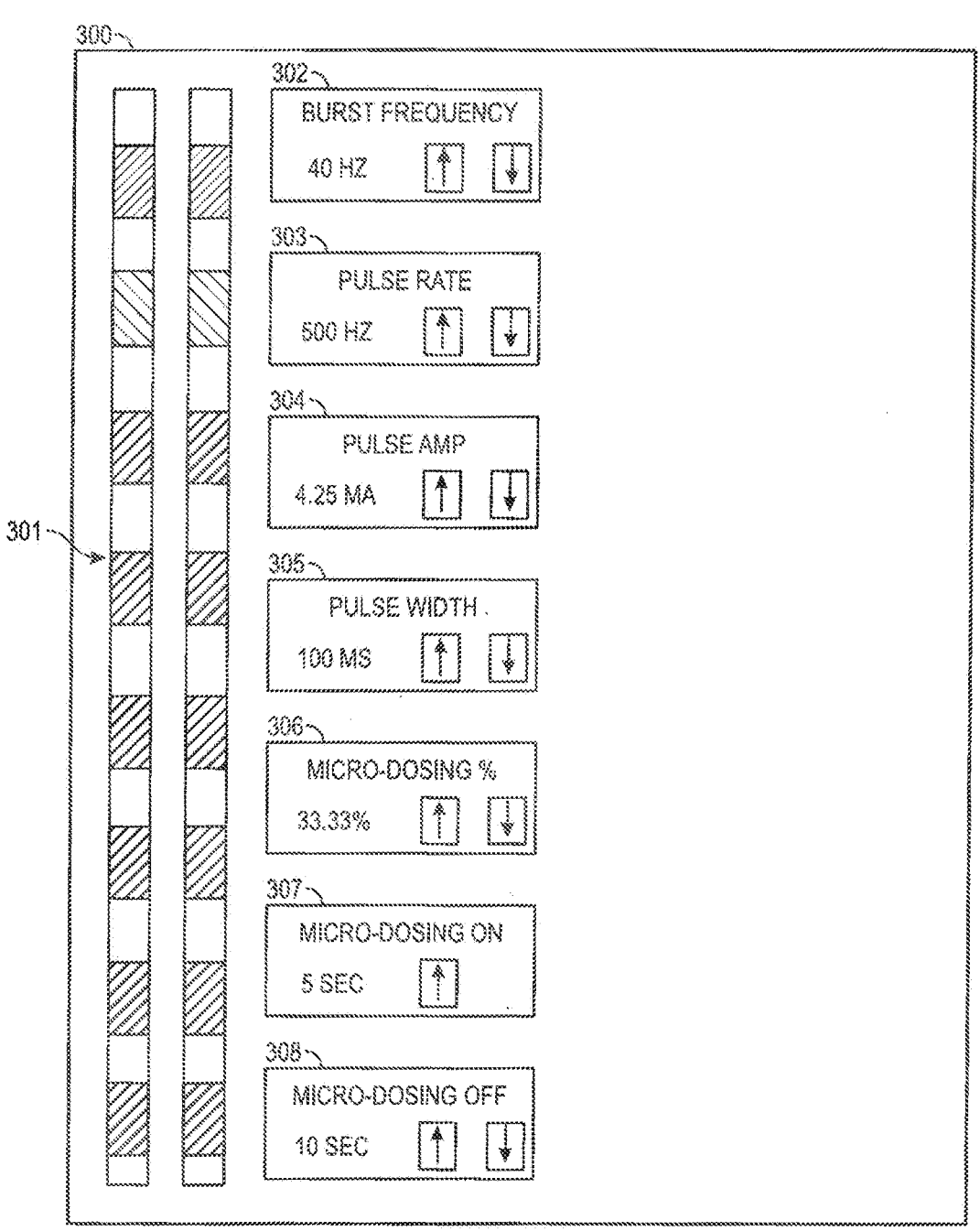
FIGS. 3 and 4 depict respective user interfaces for programming a non-paresthesia stimulation pattern according to some embodiments.

In some embodiments, a clinician defines micro-dosing or cycling parameters for a patient therapy. FIG. 3 depicts user interface screen 300 that may be presented by a clinician programmer device. The user interface screen 300 enables the clinician to apply non-paresthesia stimulation to a patient according to known parameters and cycling parameters to evaluate the patient response during the neurostimulation programming process. User interface screen 300 includes depiction 301 of one or more stimulation leads. The clinician may control the active and inactive electrode states of the lead(s) through interaction with screen 300. The clinician may control various stimulation parameters such as burst frequency, pulse rate, pulse amplitude, and pulse width using graphical user interface (GUI) controls 302-305. Although GUI controls for burst stimulation are shown in FIG. 3, any suitable GUI controls may be implemented for other non-paresthesia stimulation patterns (such as high frequency stimulation and high density stimulation as described in published literature).

The clinician may control cycling parameters using GUI controls 306-308. The clinician may control the micro-dosing percentage (equivalently the duty cycle). Upon modification of the micro-dosing percentage in GUI control 306, the clinician programmer may automatically calculate a suitable on cycle interval and a suitable off-cycle interval that correspond to the selected percentage. In some embodiments, the clinician programmer will maintain the same amount of time for the sum of the on cycle and off cycle and will modify the individual times of the on cycle and off cycle to correspond to the updated dosing percentage. After calculation, the clinician programmer then displays the respective interval times in GUI controls 307 and 308. If the clinician wishes to do so, the clinician may directly modify the one or more interval times in GUI controls 307 and 308. The clinician programmer device will update the micro-dosing percentage in GUI control 306 accordingly.

By interacting with user interface screen 300, the clinician may test stimulation applied to a patient. That is, as the clinician modifies stimulation parameters via user interface screen 300, the clinician programmer device may communicate the updated parameters to an external "trial" stimulator or to an implantable pulse generator to apply stimulation pulses to the patient. The clinician may elicit feedback from the patient during the stimulation testing to arrive at a suitable set of stimulation parameters. The clinician may also use suitable electrodes or sensors to measure relevant physiological signals to assist the selection of suitable stimulation parameters as will be discussed herein.

Figure 4:
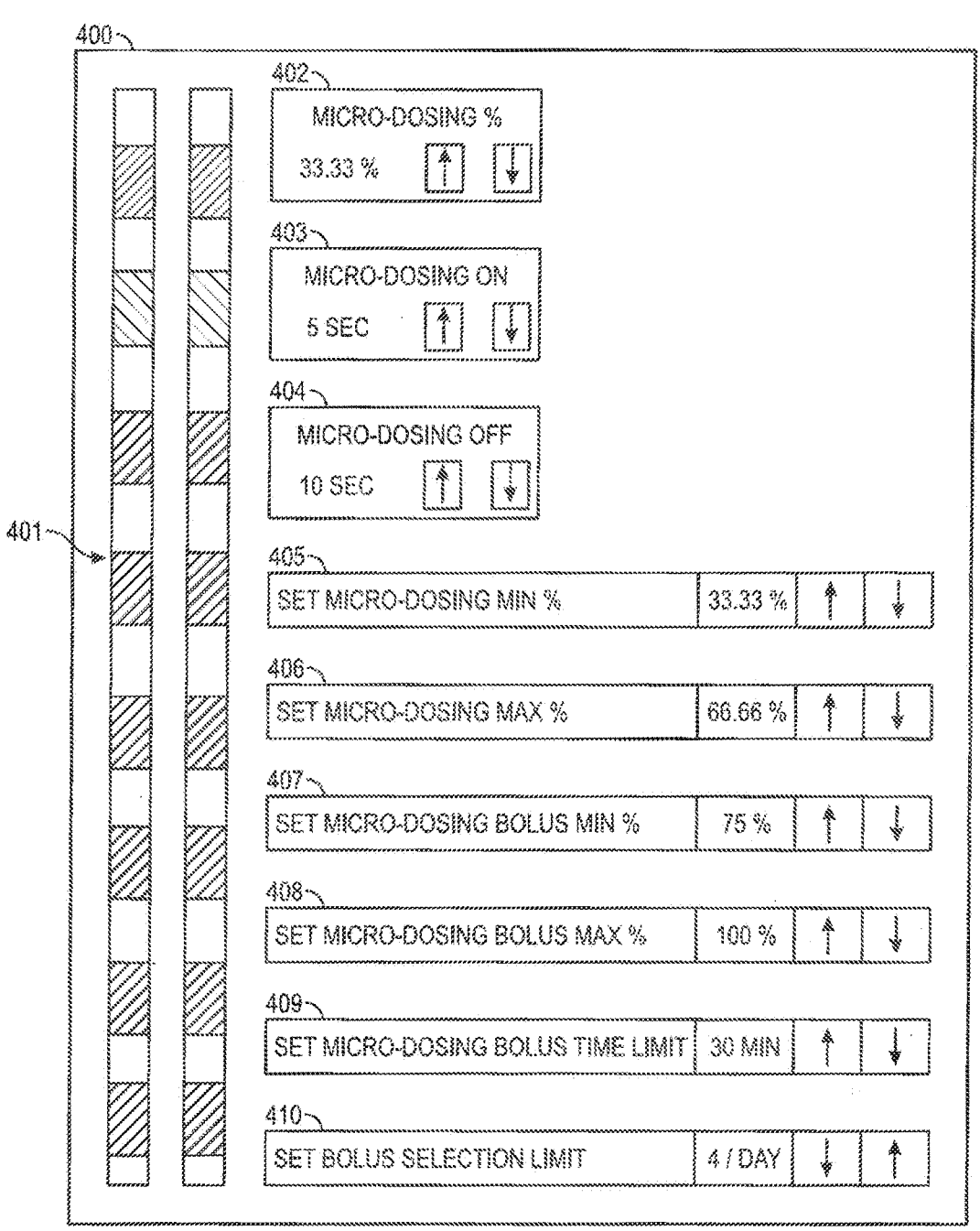

After applying test stimulation via user interface screen 300, the clinician may set micro-dosing parameters for a stimulation program using user interface screen 400 shown in FIG. 4. GUI component 401 depicts the stimulation lead with active/inactive electrode states shown (anode, cathode, inactive states for the respective electrodes). GUI components 402-404 allow control of micro-dosing percentage, micro-dosing on interval, and micro-dosing off interval values. GUI components 402-404 may be populated with the values from GUI components 306-308 as the clinician switches between user interface screens during a programming session.

User interface screen 400 includes GUI components 405 and 406 that permit the clinician to set micro-dosing minimum and maximum values for stimulation during ordinary stimulation operations. Upon completion of the programming session, the patient may change the micro-dosing percentage within this range using a patient controller device as deemed necessary by the patient.

User interface screen 400 includes GUI components 407-410 that enable a clinician to define a "bolus" stimulation mode where the micro-dosing may be temporarily increased beyond the ordinary micro-dosing maximum value. For some patients, it is possible for the patient to accommodate to a stimulation therapy, although it has been suggested that non-paresthesia burst stimulation may be less subject to accommodation than other non-paresthesia stimulation patterns. If a patient accommodates to continuous non-paresthesia stimulation, there is little modification that can be made to address the patient's sensory accommodation by only changing stimulation parameters. By providing a bolus mode of micro-dosing stimulation, some embodiments enable increased levels of non-paresthesia stimulation for periods of time, while reducing the possibility of accommodation.

GUI components 407 and 408 permit the clinician to set micro-dosing minimum and maximum percentage values for the bolus mode of operation. In some embodiments, the total amount of time for the bolus mode of stimulation will be the same as the total amount of time for the ordinary mode of stimulation and the individual times of the on cycle and off cycle are modified according to the bolus micro-dosing percentage. In other embodiments, the clinician may modify the total cycle time and/or the individual on cycle and off cycle interval times as deemed appropriate by the clinician.

GUI component 409 permits the clinician to set a time limit for an individual episode of bolus stimulation according to the increased micro-dosing duty cycling. GUI component 410 permits the clinician to control the maximum number of times that the patient may invoke the bolus mode of operation for the patient's IPG using the patient controller device.

Figure 6:
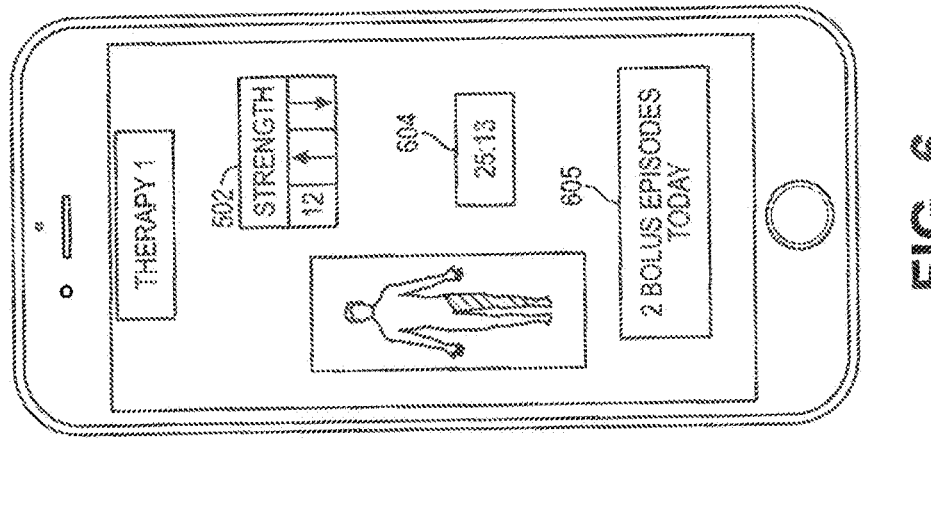
FIG. 6 depicts a user interface for controlling a patient neurostimulation therapy with a non-paresthesia stimulation pattern according to some embodiments.
Figure 5:
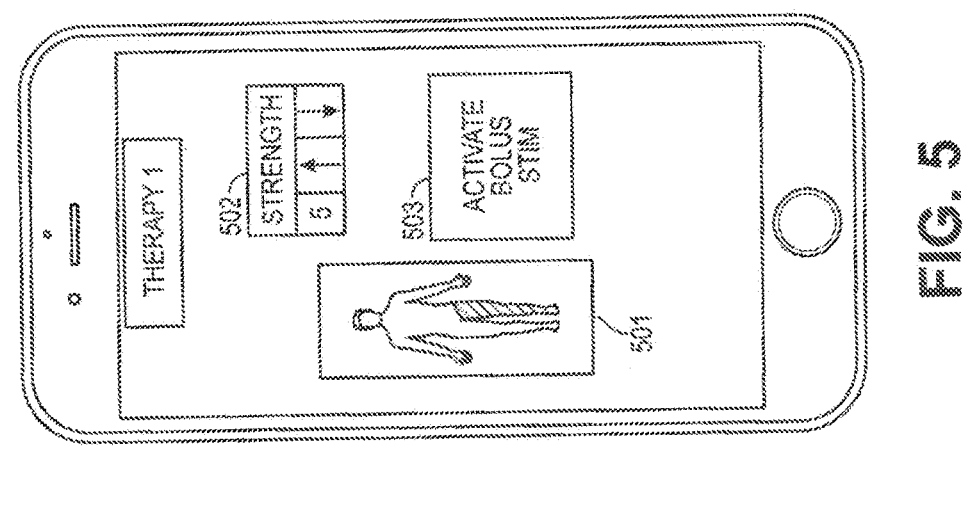
FIG. 5 depicts a user interface for controlling a patient neurostimulation therapy with a non-paresthesia stimulation pattern according to some embodiments.

When the clinician arrives at suitable parameters for programming the patient IPG, the programming parameters are transferred to the patient IPG and/or the patient controller device. FIG. 5 and FIG. 6 depict user interface screens 500 and 600 for use by a patient in controlling stimulation applied by the patient's IPG according to some embodiments. In user interface screen 500, GUI component 501 graphically displays an area of chronic pain to be addressed by the active patient therapy or program. In user interface 500, the user may adjust the stimulation level using GUI component 502. In the ordinary mode of stimulation, a range of micro-dosing or cycling percentage values is defined by the clinician. The value selected in GUI component 502 permits the patient to adjust stimulation within the range of the defined values.

The values in GUI component 502 need not correspond numerically to the permitted micro-dosing or cycling values. For example, the values in GUI component 502 may vary between a defined range (e.g., 1-10, 1-20, 1-100, etc.) and these values are then mapped to percentages within the permitted range. When the patient selects an updated micro-dosing or cycling value, the patient controller communicates the appropriate micro-dosing or cycling value(s) for communication to the patient IPG and the patient IPG applies stimulation according to the communicated value(s).

User interface 500 includes GUI component 503 to permit the patient to start an episode of bolus stimulation. When the patient touches or taps on GUI component 503, the patient controller device may transition to user interface screen 600. As shown in FIG. 6, GUI component 502 is modified to reflect the ability to increase the stimulation level while the bolus episode is ongoing. The patient may vary the stimulation level from the minimum bolus micro-dosing percentage to the maximum bolus micro-dosing percentage by modifying the value shown in GUI component 502.

In some embodiments, limitations are defined for the application of the bolus mode of stimulation. In some embodiments, the clinician defines a time limit for an individual episode of bolus stimulation. After the expiration of the time limit, the stimulation will automatically revert to stimulation within the ordinary micro-dosing limits. GUI component 604 may be included to display the amount of time remaining in the bolus mode of stimulation for an individual episode of bolus stimulation. Also, in some embodiments, the clinician may limit the number of times that bolus stimulation is permitted within a given time period. For example, the clinician may limit bolus stimulation to 1-10 times per day. GUI component 605 displays the number of bolus episodes that have been initiated by the patient for a given time period. The patient controller device may communicate a suitable message to a remote care network or a clinician system to report a number of episodes of bolus stimulation selected by the patient (e.g., whether the patient reached the maximum limit in a given day).

FIG. 7 depicts a method of applying a neurostimulation therapy of non-paresthesia to a patient according to some embodiments. In 701, test or trial stimulation is applied to patient with varying micro-dosing parameters for non-paresthesia stimulation. In 702, the clinician selects minimum and maximum micro-dosing parameters. In 703, the clinician selects minimum and maximum micro-dosing parameters for bolus stimulation. In 704, a stimulation program with micro-dosing parameters is transferred to the IPG of the patient. In 705, programming data including micro-dosing parameters is transferred to a patient controller device. In 706, electrical stimulation from the IPG is applied. The stimulation is applied under control of patient controller device where the patient controls the micro-dosing level within the defined limits by interaction with the patient controller device.

In some embodiments, a clinician may utilize sensors to monitor physiological signals that are evoked by or otherwise affected by application of non-paresthesia stimulation to determine appropriate micro-dosing or cycling parameters.

Figure 11:
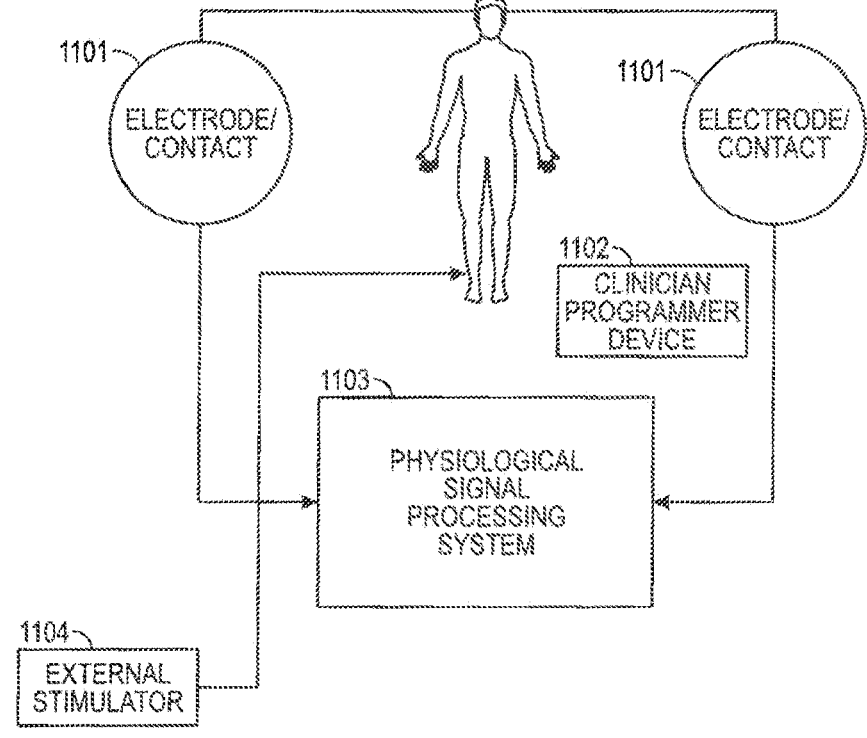
FIG. 11 depicts a system for testing a patient response to non-paresthesia stimulation to select stimulation parameters according to some embodiments.

FIG. 11 depicts system 1103 for use in determining appropriate micro-dosing or cycling parameters according to some embodiments. Sensor contacts or electrodes 1101 are placed at one or more suitable locations on the patient to capture relevant physiological signals. System 1103 includes components to sample and process the signals including analog-to-digital converters, amplifiers, and filters. Some of the components may be implemented using electronic circuitry while some of the components may be implemented in digital form on a processor, digital signal processor, ASIC, and/or the like. The system includes a display and software including user interface functions for viewing physiological waveform data, physiological waveform analysis functions, and physiological waveform data manipulation functions.

The location of the recording electrodes can also vary. In some embodiments, the recording electrodes are electrocorticography (EEG) electrodes. EEG recording refers to recording of the electrical activity of the brain from the scalp. The recorded waveforms reflect cortical electrical activity of the patient. If the EEG recording is selected by a clinician, the EEG electrodes are placed on the scalp generally above the cortex where neural activity for sensory perception occurs. EEG systems are commercially available including the Neuvo™ products from Compumedics Limited (Victoria, Australia) and Brain Vision actiCHamp™ hardware products and Brain Vision PyCorder™ software from Brain Products GmbH (Gilching Germany).

Electrical stimulation is provided to a peripheral site of the patient using external stimulator 1104. The peripheral site may be located approximate to one or more peripheral nerves (e.g., the tibial nerve). The initial stimulation may deliver stimulation strong enough to generate a stable or repeatable muscle twitch or contraction. The electrical stimulation creates somatosensory evoked potentials that travel toward the spinal cord and the brain. The somatosensory evoked potentials are detected using the EEG electrodes 1101 and suitable signal analysis is applied using system 1103.

While the peripheral stimulation is applied, spinal cord stimulation or DRG stimulation is applied to the patient using one or more non-paresthesia stimulation patterns by communicating suitable stimulation parameters to the patient's implantable pulse generator (not shown in FIG. 11) using clinician programmer 1102 or via a trial stimulator. It has been demonstrated that spinal cord stimulation interferes with the transmission of SEPs (inhibition of somatosensory evoked potentials during spinal cord stimulation and its possible role in the comprehension of antalgic mechanisms of neurostimulation for neuropathic pain. Minerva Anestesiologica [1 Mar. 2012, 78(3):297-302, Buonocore et al., which is incorporated herein by reference) by either suppressing or abolishing the SEPs signal.

The peripheral stimulation is applied in a manner that the peripheral stimulation affects the dermatome or sub-dermatomal regions where the patient perceives chronic pain. If this is not possible due to the hyperalgesic effect of chronic pain, another area (either ipsi or contralateral) whose sensory fibers project through the same path of the fibers projecting from the painful area may be used. While a full EEG set up can be used, it is also possible to use only two electrodes (a recording and a reference) with the recording electrode strategically placed over the ideal region to record the SEPs produced by sensory stimulation.

EEG recording is performed while non-paresthesia stimulation is applied to the patient. One or more recording electrodes 1101 are used to record the evoked response. The signal will be amplified, band-pass filtered and stored. A suitable number of repetitions will be delivered and the recorded responses averaged to improve signal to noise ratio.

The evoked response data will be characterized in the original shape and/or after further processing including but not limited to rectification, band passing, integration, derivation and combinations of thereof. Characterization of the evoked responses will be performed in one or multiple ways including but not limited to positive and negative deflection (s) size, delay and width, peak to peak size and delay, energy under the curve, principal component analysis, machine learning, fuzzy logic and combinations of thereof. In some embodiments, the size of the averaged evoked potential will be characterized by measuring the peak to peak amplitude of the deflections expected given the specific stimulation/recording electrodes setup. A reference SEP can be obtained in absence of stimulation to identify the location of the peaks when not known in advance.

Non-paresthesia stimulation will be delivered with settings known to produce optimal pain relief and the corresponding SEP will be characterized. These settings used for reference may include continuous stimulation, i.e., a non-paresthesia stimulation pattern without "off" cycle intervals. After obtaining the reference response, SCS micro-dosing or cycling percentage will be decreased progressively and for each ratio a new SEP will be collected until the evoked SEP will show a significant increase in size indicating that non-paresthesia stimulation may be starting to lose efficacy. The clinician may select one or more micro-dosing OFF/ON parameters by identifying the largest micro-dosing or cycling percentage where the SEP was not significantly different from the SEP obtained using the setting known to provide optimal pain relief (e.g., a continuous non-paresthesia stimulation pattern). A statistically equivalent SEP characterization between micro-dosing SEP data and reference SEP data shall occur when a comparison of one or more SEP characterization parameters between the micro-dosing and reference SEP are within a predetermined threshold of one another. The threshold may be selected according to a clinician and, for example, may be selected from 20%, 15%, 10%, or 5% difference in micro-dosing and reference SAP data in some embodiments.

In other embodiments, physiological signals may be sampled by an implantable neurostimulation system and processed to identify appropriate micro-dosing or cycling parameters. In some embodiments, evoked compound action potentials are sampled using the system described in U.S. Pat. No. 9,931,510, which is incorporated herein by reference. The electrodes used to acquire SAP signals can be the electrodes of one or more stimulation leads of a neurostimulation system implanted in the patient (see FIG. 8).

FIGS. 12A-12D illustrate sensory action potential (SAP) activity data 1540-1546 that is obtained when the SAP signals 1502-1508, respectively, are analyzed. Electrodes of one or more stimulation leads may be used to acquire the SAP electrical signals for sampling, digitization, processing, etc. The SAP activity may be obtained and processed using IPG 850 that includes suitable sampling circuitry, software, and one or more processors. In alternative embodiments, IPG 850 samples the SAP activity and the signal processing is performed by software and one or more processors of external device 860. The activity data 1540-1546 is divided into activity data segments 1548-1562. For example, the activity data 1540 shown in FIG. 12A includes first and second SAP activity data segments 1548 and 1550. The first activity data segment 1548 may also be referred to as a pre-therapy activity data segment 1548, as the SAP sample window 1510 occurs before delivery of the burst stimulation waveform during window 1528. The second activity data segment 1550 may also be referred to as a post-therapy activity data segment 1550, as the SAP sample window 1514 occurs after delivery of the burst stimulation waveform during window 1528. Likewise, the activity data 1542-1546 shown in FIGS. 12B-12D, respectively, are also partitioned into pre-therapy activity data segments 1552, 1556 and 1560, and post-therapy activity data segments 1554, 1558 and 1562. Similar to the burst stimulation waveform delivery window 1528 shown in FIG. 12A, burst stimulation waveform delivery windows 1530, 1532 and 1534 are exemplified in FIGS. 12B-12D, respectively, wherein each burst stimulation delivery window is disposed between the corresponding pre-therapy and post-therapy activity data segments. It should be noted that the reference numeral ranges used in this paragraph only include even reference numbers unless otherwise noted.

The pre- and post-therapy activity data segments 1548-1562 are divided into temporal bins 1568, each bin of which corresponds to a temporal portion of the SAP signals 1502-1508. The data segments 1548-1562 include counts 1564 of the number of peaks or spikes in the corresponding SAP signal 1502-1508 for the corresponding temporal bin 1568. The counts 1564 correspond to the number of neuronal firings evoked by the sensory input. It should be noted that the reference numeral ranges used in this paragraph only include even reference numbers unless otherwise noted.

Figure 12A:
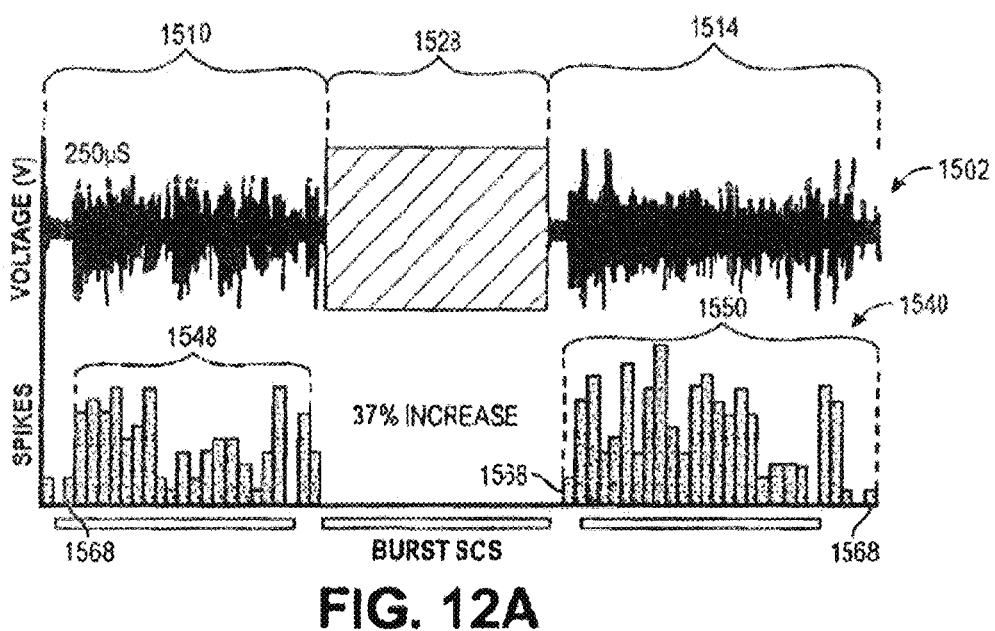
FIGS. 12A-12D depict neuronal activity affected by burst stimulation according to some embodiments.
Figure 12B:
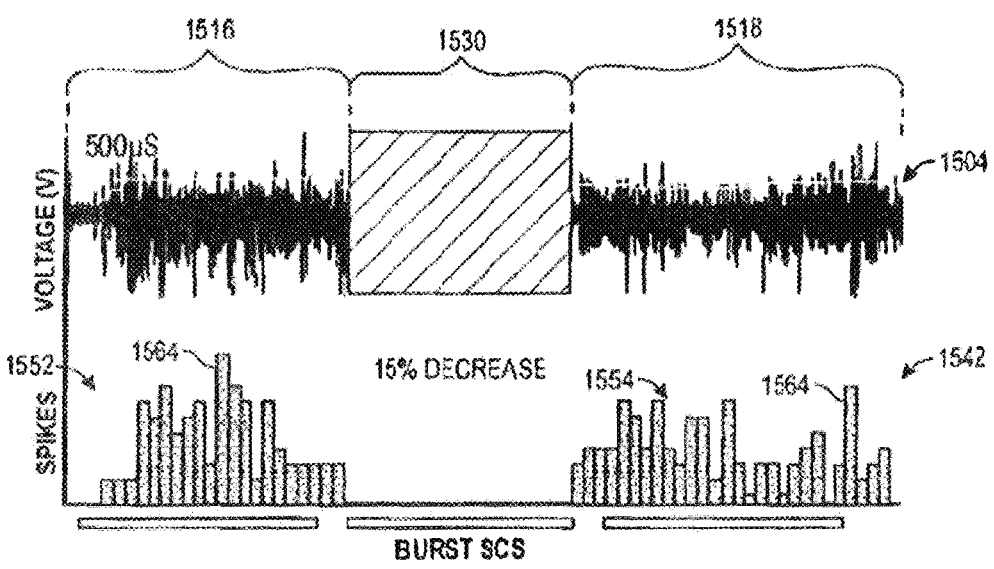
Figure 12C:
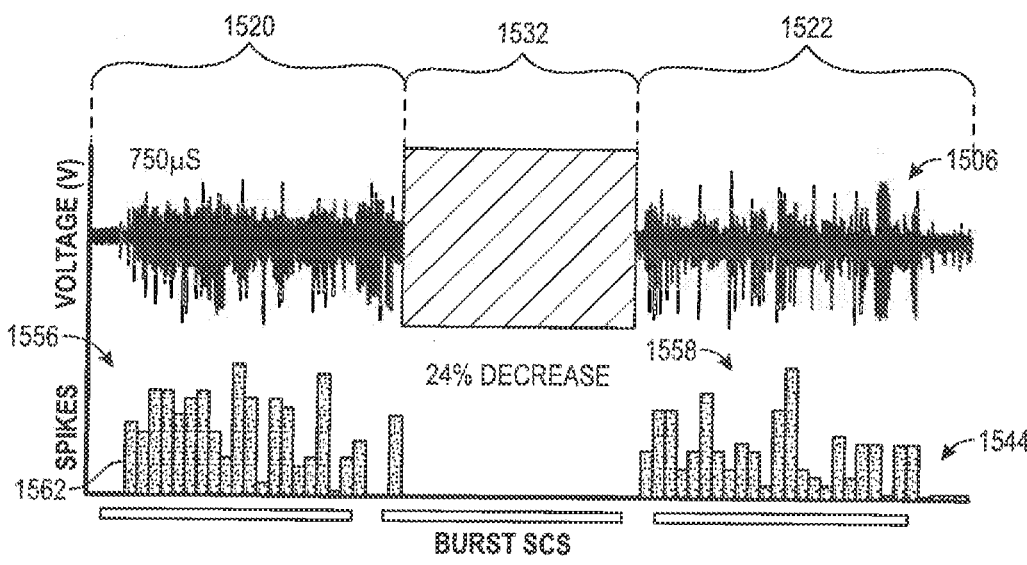
Figure 12D:
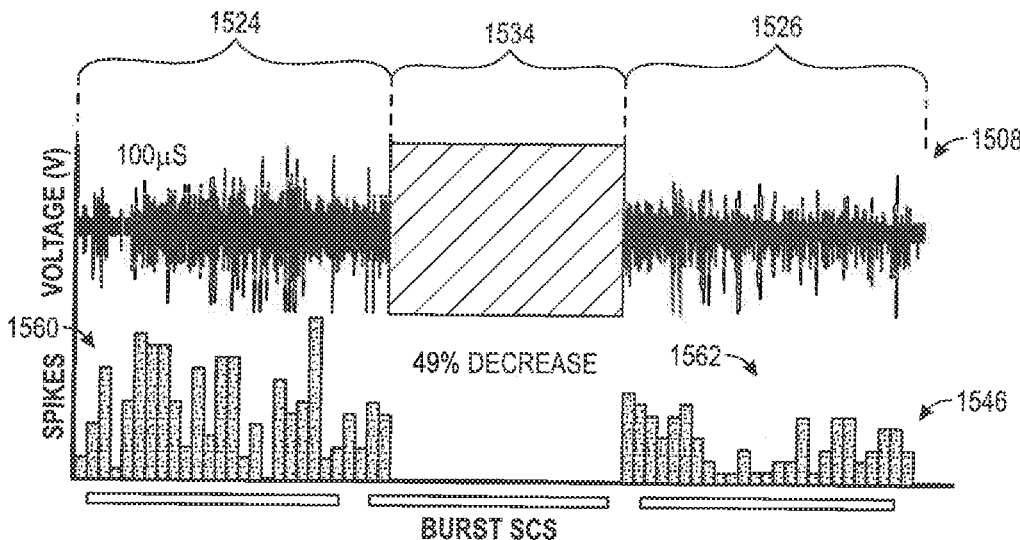

The data segments 1552, 1556 and 1560 exhibit high counts 1564 within a majority of the bins 1568, as compared to the data segments 1554, 1558 and 1562 which exhibit lower count 1564 within a majority of the bins 1568. The frequency/count 1564 may be summed for each single data segment 1548-1562 and each pre-therapy activity data segment compared to the related post-therapy activity data segment (e.g., data segment 1548 compared to 1550) to determine a change in activity. By way of example, the sum of the count 1564 of spikes in the post-therapy activity data segment 1554 (corresponding to the SAP sample window 1518) exhibits a 15% decrease in the count of spikes, as compared to the sum of the count of spikes in the pre-therapy activity data segment 1552 (corresponding to the SAP sample window 1516), as illustrated in FIG. 12B. The sum of the count 1564 of spikes in the post-therapy activity data segment 1558 (corresponding to the SAP sample window 1522) exhibits a 24% decrease in the count of spikes, as compared to the sum of the count of spikes in the pre-therapy activity data segment 1556 (corresponding to the SAP sample window 1520), as illustrated in FIG. 12C. The sum of the count 1564 of spikes in the post-therapy activity data segment 1562 (corresponding to the SAP sample window 1526) exhibits a 49% decrease in the count of spikes, as compared to the sum of the count of spikes in the pre-therapy activity data segment 1560 (corresponding to the SAP sample window 1524), as illustrated in FIG. 12D. It should be noted that the reference numeral ranges used in this paragraph only include even reference numbers unless otherwise noted.

When the counts 1564 in the activity data segments 1552, 1556 and 1560 are compared to the counts 1564 in the activity data segments 1554, 1558 and 1562, it is seen that the sensory action potential (as measured in the SAP signals 1504-1508) was reduced/attenuated after delivery of the burst stimulation waveforms by varying degrees. The degree to which the sensory action potential was attenuated is dependent, at least in part, on the burst therapy parameters. When no burst stimulation waveforms are delivered, the frequency content of the sensory action potential measured over the A-delta and C-fibers is higher. After delivery of a burst stimulation waveform, the sensory action potentials are suppressed and the frequency content of SAP decreased. As explained herein, methods and systems are provided to determine and control therapy parameter sets for burst and/or high frequency stimulation waveforms based on closed loop sensory measurement. It should be noted that the reference numeral ranges used in this paragraph only include even reference numbers unless otherwise noted.

In some embodiments, non-paresthesia stimulation is applied to a patient using IPG 850 and SAP data is processed to identify appropriate micro-dosing or cycling parameters. FIG. 13 depicts a method for determining appropriate micro-dosing or cycling parameters according to some embodiments. In some embodiments, the operations of FIG. 13 are performed by a clinician programmer device in communication with an implantable pulse generator. For example, the operations may be performed by, or under directions from, one or more processors when executing program instructions. In other embodiments, clinician personnel may perform selected operations.

In 1301, test stimulation is applied to patient with varying micro-dosing parameters for non-paresthesia stimulation. The test stimulation may include a reference non-paresthesia stimulation pattern that is continuous (i.e., has no "stimulation-off" intervals). Additionally, or alternatively, the reference stimulation may include a non-paresthesia stimulation pattern that has previously determined to be of interest (e.g., an optimal stimulation pattern for the patient). The application of the test stimulation may be performed by communication of suitable control signals from a clinician controller device to an implantable pulse generator.

In 1302, SAP data is measured for non-paresthesia stimulation applied with varying micro-dosing parameters. In 1303, the SAP data is processed to extract neural activity for A-delta and C-fibers (e.g., using signal power for the relevant neural frequencies). The SAP data may be processed by applying frequency filtering of SAP data as described in U.S. Pat. No. 9,931,510. In 1304, the micro-dosing percentage is determined where extracted neural activity satisfies one or more therapy constraints. This operation may include identifying a lowest one cycling parameter that has power corresponding to A-delta and C-fibers that differ within a predetermined amount from power corresponding to A-delta and C-fibers in SAP data for the reference non-paresthesia stimulation. A therapy constraint of a difference of 20%, 15%, 10%, or 5% from the SAP data for the reference non-paresthesia stimulation pattern may be applied according to a selection of the clinician.

In 1305, the therapy micro-dosing parameters are set for the patient device according to the determined micro-dosing percentage. The patient then uses the patient system to apply non-paresthesia stimulation according to embodiments described herein.

Figure 8:
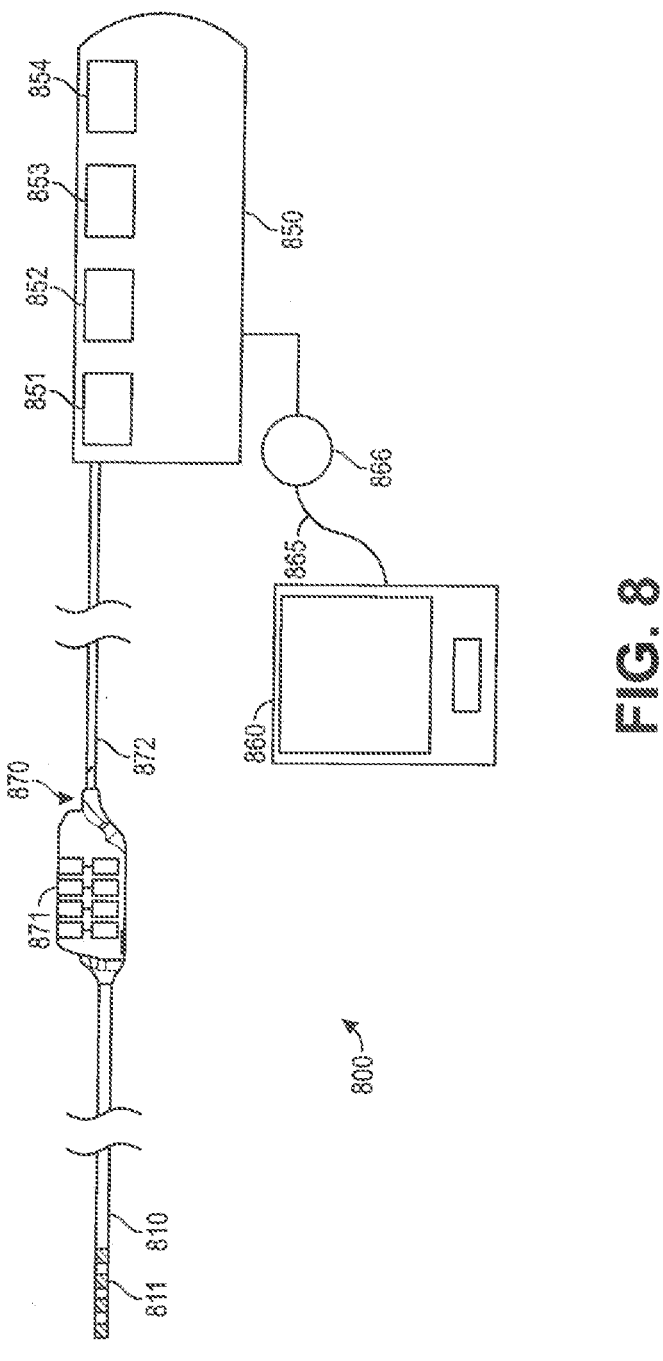
FIG. 8 depicts a neurostimulation system that may be adapted according to some embodiments.

FIG. 8 depicts a neurostimulation system that may be employed according to some embodiments. Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Under certain stimulation conditions, applying electrical energy to the spinal cord associated with regions of the body afflicted with chronic pain can induce "paresthesia" (a subjective sensation of numbness or tingling) in the afflicted bodily regions. Certain stimulation patterns (such as BurstDR™ stimulation provided by pulse generators of Abbott) modulate neural activity to reduce chronic pain without inducing paresthesia.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Stimulation system 800 generates electrical pulses for application to tissue of a patient, or subject, according to one embodiment. Stimulation system 800 includes an implantable pulse generator (IPG) 850 that is adapted to generate electrical pulses for application to tissue of a patient. Implantable pulse generator 850 typically includes a metallic housing that encloses a controller 851, pulse generating circuitry 852, a battery 853, far-field and/or near field communication circuitry 854, and other appropriate circuitry and components of the device. Controller 851 typically includes a microcontroller or other suitable processor for controlling the various other components of the device. Software code is typically stored in memory of implantable pulse generator 850 for execution by the microcontroller or processor to control the various components of the device (e.g., code to implement operations discussed herein). The software code stored in memory of pulse generator 850 may support operations of embodiments disclosed herein.

Implantable pulse generator 850 may comprise one or more attached extension components 870 or be connected to one or more separate extension components 870. Alternatively, one or more stimulation leads 810 may be connected directly to implantable pulse generator 850. Within implantable pulse generator 850, electrical pulses are generated by pulse generating circuitry 852 and are provided to switching circuitry. The switching circuit connects to output wires, traces, lines, or the like (not shown) which are, in turn, electrically coupled to internal conductive wires (not shown) of a lead body 872 of extension component 870. The conductive wires, in turn, are electrically coupled to electrical connectors (e.g., "Bal-Seal" connectors) within connector portion 871 of extension component 870. The terminals of one or more stimulation leads 810 are inserted within connector portion 871 for electrical connection with respective connectors. Thereby, the pulses originating from implantable pulse generator 850 and conducted through the conductors of lead body 872 are provided to stimulation lead 810. The pulses are then conducted through the conductors of stimulation lead 810 and applied to tissue of a patient via electrodes 811. Any suitable known or later developed design may be employed for connector portion 871.

For implementation of the components within implantable pulse generator 850, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 850. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 810 may include a lead body of insulative material about a plurality of conductors within the material that extend from a proximal end of stimulation lead 810 to its distal end. The conductors electrically couple a plurality of electrodes 811 to a plurality of terminals (not shown) of stimulation lead 810. The terminals are adapted to receive electrical pulses and the electrodes 811 are adapted to apply stimulation pulses to tissue of the patient. Also, sensing of physiological signals may occur through electrodes 811, the conductors, and the terminals. Additionally, or alternatively, various sensors (not shown) may be located near the distal end of stimulation lead 810 and electrically coupled to terminals through conductors within the lead body 872. Stimulation lead 810 may include any suitable number of electrodes 811, terminals, and internal conductors.

Figure 9A:
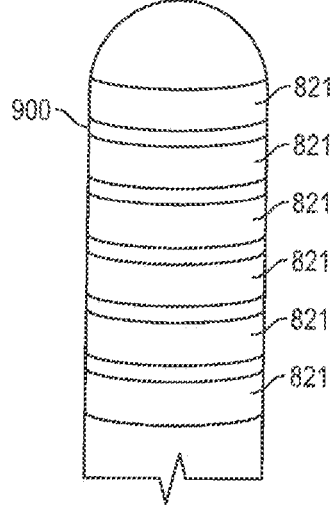
FIGS. 9A-9C depict neurostimulation leads that may be used in the system of FIG. 8.
Figure 9B:
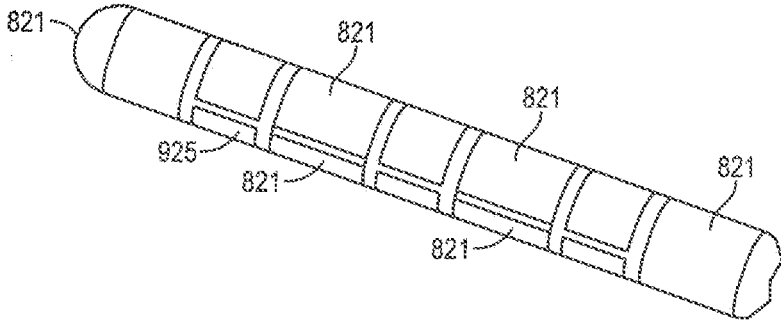
Figure 9C:
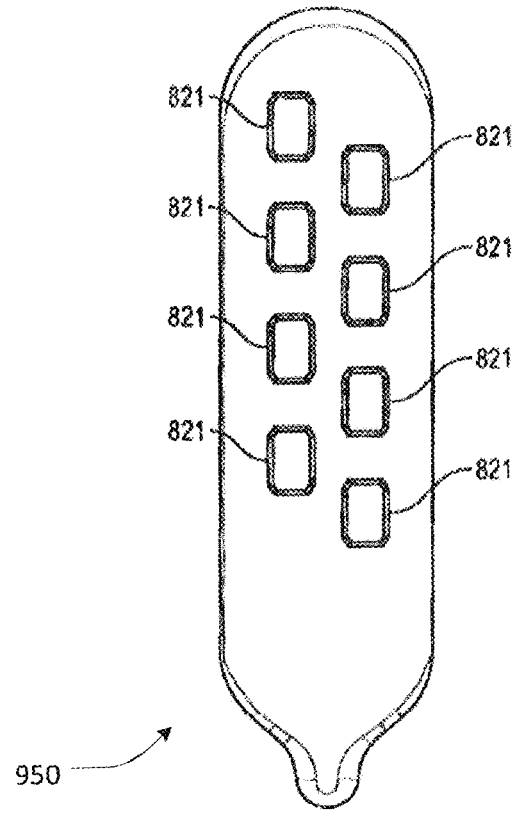

FIGS. 9A-9C respectively depict stimulation portions 900, 925, and 950 for inclusion at the distal end of stimulation lead 110. Stimulation portions 900, 925, and 950 each include one or more electrodes 821. Stimulation portion 900 depicts a conventional stimulation portion of a "percutaneous" lead with multiple ring electrodes. Stimulation portion 925 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 950 includes multiple planar electrodes on a paddle structure.

Controller device 860 (shown in FIG. 8) may be implemented to recharge battery 853 of implantable pulse generator 850 (although a separate recharging device could alternatively be employed). A "wand" 865 may be electrically connected to controller device 860 through suitable electrical connectors (not shown). The electrical connectors are electrically connected to a "primary" coil 866 at the distal end of wand 865 through respective wires (not shown). Typically, primary coil 866 is connected to the wires through capacitors (not shown). Also, in some embodiments, wand 865 may comprise one or more temperature sensors for use during charging operations.

The patient then places the primary coil 866 against the patient's body immediately above the secondary coil (not shown), i.e., the coil of the implantable medical device. Preferably, the primary coil 866 and the secondary coil are aligned in a coaxial manner by the patient for efficiency of the coupling between the primary and secondary coils. Controller device 860 generates an AC-signal to drive current through primary coil 866 of wand 865. Assuming that primary coil 866 and secondary coil are suitably positioned relative to each other, the secondary coil is disposed within the field generated by the current driven through primary coil 866. Current is then induced in secondary coil. The current induced in the coil of the implantable pulse generator is rectified and regulated to recharge battery of implantable pulse generator 850. The charging circuitry may also communicate status messages to controller device 860 during charging operations using pulse-loading or any other suitable technique. For example, controller device 860 may communicate the coupling status, charging status, charge completion status, etc.

External controller device 860 is also a device that permits the operations of implantable pulse generator 850 to be controlled by user after implantable pulse generator 850 is implanted within a patient, although in alternative embodiments separate devices are employed for charging and programming. Also, multiple controller devices may be provided for different types of users (e.g., the patient or a clinician).

Controller device 860 can be implemented by utilizing a suitable handheld processor-based system that possesses wireless communication capabilities. Software is typically stored in memory of controller device 860 to control the various operations of controller device 860 (e.g., code to implement operations discussed herein). The software code stored in memory of device 860 may support the operations according to embodiments disclosed herein. Also, the wireless communication functionality of controller device 860 can be integrated within the handheld device package or provided as a separate attachable device. The user interface functionality of controller device 860 is implemented using suitable software code for interacting with the user and using the wireless communication capabilities to conduct communications with implantable pulse generator 850.

Controller device 860 preferably provides one or more user interfaces to allow the user to operate implantable pulse generator 850 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 850 modifies its internal parameters in response to the control signals from controller device 860 to vary the stimulation characteristics of stimulation pulses transmitted through stimulation lead 810 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Pulse generator device 850 and controller device 860 may be adapted to apply different types of neurostimulation. One or more stimulation sets or programs may be defined with tonic stimulation. Also, these devices may support burst stimulation as disclosed in U.S. Pat. No. 8,934,981 which is incorporated herein by reference. In burst stimulation, groups of pulses are provided at a relatively high frequency (greater than 250 Hz) with adjacent groups of pulses separated by a quiet period. The groups are repeated at a relatively lower frequency (e.g., 40 Hz or other physiologically relevant frequencies). These devices may support "noise" stimulation such as described in U.S. Pat. No. 9,498,634, which is incorporated herein by reference. These devices may also support high frequency stimulation (e.g., 1500 Hz-20,000 Hz).

Example commercially available neurostimulation systems include the PROTEGE™, PRODIGY™, PROCLAIM™, INFINITY™ pulse generators and CLINICIAN PROGRAMMER APP from Abbott Laboratories. Example commercially available stimulation leads include the QUATTRODE™, OCTRODE™, AXXESS™, LAMITRODE™, TRIPOLE™, EXCLAIM™, PENTA™ and INFINITY™ stimulation leads from Abbott Laboratories. Commercially available devices may be modified according to one or more embodiments described in this application.

Figure 10:
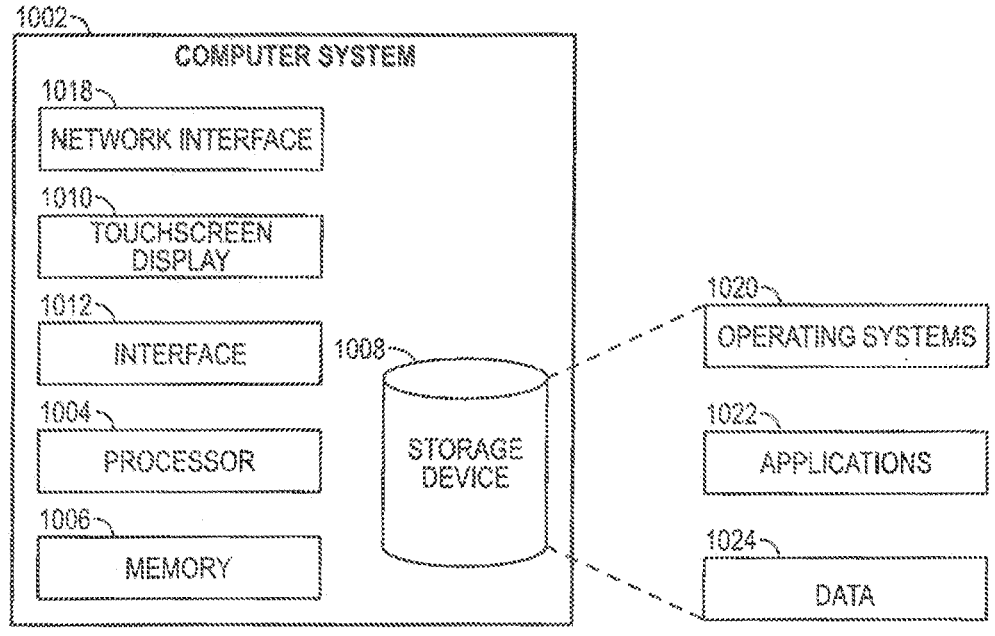
FIG. 10 depicts a processor-based system that may be employed for a clinician programmer device or a patient controller device according to some embodiments.

FIG. 10 illustrates one embodiment of a computer system (e.g., patient controller or clinician programmer device) 1002 that facilitates medical device management in accordance with some embodiments. Computer system 1002 includes processor 1004, memory 1006, storage device 1008, touch screen display 1010, interface components 1012. Computer system 1002 includes network interface 1018 for conducting network communications.

Memory 1006 can include a volatile and non-volatile memory. Storage device 1008 can store operating system 1020, device management applications 1022 for management of implantable devices and provision of remote medical care, and data 1024. Device management applications 1022 may include applications with software code to perform operations discussed herein including communication with patient controller devices, communication with clinician programmer devices, validation of therapeutic data from clinician programming, analysis of programming data, auditing operations, distribution of revocation data, and any other appropriate device management operations.

Computer system 1002 may also store and access data through a cloud computing architecture with relevant data distributed across multiple platforms at different physical locations. Data 1024 can include any data relevant to patients, medical devices, physiological data, therapeutic settings, clinicians, and clinician devices for the management of medical devices, monitoring of patient status, detection of patient conditions, and any other task related to remote monitoring and management of health care for patients with medical devices. Data 1024 may include any of the data discussed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the hardware modules can include, but are not limited to, application-specific integrated circuit (ASIC) chips, field-programmable gate arrays (FPGAs), and other program-mable-logic devices now known or later developed. When the hardware modules are activated, the hardware modules perform the methods. One or more of the operations described above in connection with the methods may be performed using one or more processors. The different devices in the systems described herein may represent one or more processors, and two or more of these devices may include at least one of the same processors. In one embodi-ment the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various com-mands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous pro-cessing, or in response to a request made by another pro-cessing machine.

The controller may include any processor-based or micro-processor-based system including systems using microcon-trollers, reduced instruction set computers (RISC), applica-tion specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally, or alternatively, the controllers and the controller device may represent circuits that may be implemented as hardware. The above examples are exemplary only and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed there-after and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention with-out departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "compris-ing" and "wherein." Moreover, in the following claims, the terms "first," "second," and "third," etc. are used merely as labels, and are not intended to impose numerical require-ments on their objects. Further, the limitations of the fol-lowing claims are not written in means-plus-function format and are not intended to be interpreted based on 45 U.S.C. § 112(f), unless and until such claim limitations expressly use the phrase "means for" followed by a statement of function void of further structure and processes included within the hardware modules.

The invention claimed is:

1. A method of providing a neurostimulation therapy to a patient using a non-paresthesia stimulation pattern, the method comprising:

communicating one or more first control signals from a patient controller device to an implantable pulse gen-erator to provide stimulation pulses for a regular mode of stimulation;

operating the implantable pulse generator, in response to the one or more first control signals, to apply stimula-tion pulses to nerve tissue of the patient using the non-paresthesia stimulation pattern with interleaved stimulation-on intervals and stimulation-off intervals arranged according to a first cycling parameter for the regular mode of stimulation;

communicating one or more second control signals from the patient controller device to the implantable pulse generator to provide stimulation pulses for a bolus mode of operation; and operating the implantable pulse generator, in response to the one or more second control signals, to apply stimu-lation pulses to the nerve tissue of the patient using the non-paresthesia stimulation pattern with the interleaved stimulation-on intervals and stimulation-off intervals arranged according to a second cycling parameter for the bolus mode of stimulation, wherein the second cycling parameter provides greater relative provision of pulses of the non-paresthesia stimulation pattern than the first cycling parameter.

2. The method of claim 1 wherein the patient controller device provides one or more user interface controls to allow the patient to select the first cycling parameter from a range of permitted values.

3. The method of claim 1 wherein the patient controller device provides one or more user interface controls to allow the patient to select the second cycling parameter from a range of permitted values.

4. The method of claim 1 wherein the bolus mode of operation is limited to a predetermined amount of time.

5. The method of claim 4 wherein the implantable pulse generator automatically reverts to the regular mode of operation from the bolus mode of operation at an end of the predetermined amount of time.

6. The method of claim 1 wherein the patient controller device limits a number of episodes of the bolus mode of operation per day according to a clinician parameter.

7. The method of claim 1 wherein the patient controller device communicates a signal to a remote care network or a clinician system that the patient has selected a number of bolus episodes.

8. The method of claim 1 wherein the non-paresthesia stimulation patterns are burst stimulation patterns that include groups of pulses separated by quiescent intervals.

9. The method of claim 1 wherein the non-paresthesia stimulation patterns are high frequency stimulation patterns with a pulse repetition rate of at least 1,200 hertz (Hz).

10. The method of claim 1 wherein the interleaved stimulation-on intervals and stimulation-off intervals are longer than one second.

11. A system for providing a neurostimulation therapy to a patient using a non-paresthesia stimulation pattern, the system comprising:

an implantable pulse generator (IPG) for providing stimulation pulses to tissue of the patient using the non-paresthesia stimulation pattern, the IPG comprising: a processor for controlling operations of the IPG, pulse generating circuitry, and wireless communication circuitry; and a patient controller device for communicating with the IPG to control provision of the neurostimulation therapy to the patient, wherein the patient controller device comprises: a processor for controlling the patient controller device, wireless communication circuitry for communicating with the IPG, and one or more user interface components for interacting with the patient;

wherein the patient controller device is adapted to receive a first input from the patient to control the neurostimulation therapy according to a regular mode of operation and, in response to receiving the first input, to communicate one or more first control signals from the patient controller device to the IPG to provide stimulation pulses for the regular mode of operation using the non-paresthesia stimulation pattern with interleaved stimulation-on intervals and stimulation-off intervals arranged according to a first cycling parameter;

wherein the patient controller device is adapted to receive a second input from the patient to control the neurostimulation therapy according to a bolus mode of operation and, in response to receiving the second input, to communicate one or more second control signals from the patient controller device to the IPG to provide stimulation pulses for the bolus mode of operation using the non-paresthesia stimulation pattern with the interleaved stimulation-on intervals and stimulation-off intervals arranged according to a second cycling parameter;

wherein the second cycling parameter provides greater relative provision of pulses of the non-paresthesia stimulation pattern than the first cycling parameter.

12. The system of claim 11 wherein the patient controller device provides one or more user interface controls to allow the patient to select the first cycling parameter from a range of permitted values.

13. The system of claim 11 wherein the patient controller device provides one or more user interface controls to allow the patient to select the second cycling parameter from a range of permitted values.

14. The system of claim 11 wherein the bolus mode of operation is limited to a predetermined amount of time.

15. The system of claim 14 wherein the IPG automatically reverts to the regular mode of operation from the bolus mode of operation at an end of the predetermined amount of time.

16. The system of claim 11 wherein the patient controller device limits a number of episodes of bolus mode of operation per day according to a clinician parameter.

17. The system of claim 11 wherein the patient controller device communicates a signal to a remote care network or a clinician system that the patient has selected a number of bolus episodes.

18. The system of claim 11 wherein the non-paresthesia stimulation patterns are burst stimulation patterns that include groups of pulses separated by quiescent intervals.

19. The system of claim 11 wherein the first cycling parameter includes a first duty cycle associated with the interleaved stimulation-on intervals and stimulation-off intervals for application of the non-paresthesia stimulation pattern, and wherein the second cycling parameter includes a second duty cycle associated with the interleaved stimulation-on intervals and stimulation-off intervals for application of the non-paresthesia stimulation pattern, the second duty cycle greater than the first duty cycle.

20. The system of claim 11, wherein the IPG is further configured apply the non-paresthesia stimulation pattern, during both the regular mode and the bolus mode, without inducing perception of paresthesia in the patient.

* * * * *